(12) United States Patent
Lavallee et al.

(10) Patent No.: US 9,684,768 B2
(45) Date of Patent: Jun. 20, 2017

(54) SYSTEM AND METHOD FOR DETERMINING AN OPTIMAL TYPE AND POSITION OF AN IMPLANT

(71) Applicant: OMNIlife science, Inc., Raynham, MA (US)

(72) Inventors: Stephane Lavallee, Saint Martin d'Uriage (FR); Carinne Granchi, New York, NY (US); Laurence Vertallier, La Tronche (FR); Christopher Plaskos, Plymouth, MA (US)

(73) Assignee: OMNIlife science, Inc., Raynham, MA (US)

( * ) Notice: Subject to any disclaimer, the term of this patent is extended or adjusted under 35 U.S.C. 154(b) by 0 days.

(21) Appl. No.: 14/666,001

(22) Filed: Mar. 23, 2015

(65) Prior Publication Data

US 2015/0193591 A1 Jul. 9, 2015

Related U.S. Application Data

(63) Continuation of application No. 13/540,134, filed on Jul. 2, 2012, now Pat. No. 8,990,052, which is a
(Continued)

(51) Int. Cl.
*G06F 19/00* (2011.01)
*G06F 17/50* (2006.01)
(Continued)

(52) U.S. Cl.
CPC .......... *G06F 19/3437* (2013.01); *A61B 34/10* (2016.02); *A61B 34/20* (2016.02);
(Continued)

(58) Field of Classification Search
CPC ......... A61B 19/50; A61B 19/56; G06F 17/50; G06F 19/3437
(Continued)

(56) References Cited

U.S. PATENT DOCUMENTS 5,564,437 A 10/1996 Bainville et al.
5,682,886 A * 11/1997 Delp .................... A61B 17/154
128/920

(Continued)

FOREIGN PATENT DOCUMENTS

EP 0920838 9/1999
FR 2775889 9/1999
(Continued)

OTHER PUBLICATIONS

<http://en.wikipedia.org/wiki/Levenberg-Marquardt_algorithm>, last modified Nov. 15, 2007.
(Continued)

*Primary Examiner* — Christopher Beccia
(74) *Attorney, Agent, or Firm* — Kim Winston, LLP

(57) ABSTRACT

A computer-assisted orthopedic surgery system includes a device for generating a three dimensional geometrical surface model of a first bone and a database containing three 3 dimensional implant models of a plurality of available implants. The system includes a computer that is configured to permit a user to select from the database a first implant and display on a screen the three dimensional implant model of the first implant. The computer superimposes on the screen the implant model on top of the model of the first bone such that the two models are visually identifiable from one another.

19 Claims, 4 Drawing Sheets

Related U.S. Application Data continuation of application No. 11/955,160, filed on Dec. 12, 2007, now Pat. No. 8,214,016.

(60) Provisional application No. 60/869,668, filed on Dec. 12, 2006.

(51) Int. Cl.
  *A61B 34/10* (2016.01)
  *A61B 34/20* (2016.01)
  *A61B 34/00* (2016.01)
  *A61B 90/00* (2016.01)

(52) U.S. Cl.
  CPC ............ *G06F 17/50* (2013.01); *A61B 34/25* (2016.02); *A61B 2034/102* (2016.02); *A61B 2034/105* (2016.02); *A61B 2034/108* (2016.02); *A61B 2034/2055* (2016.02); *A61B 2034/256* (2016.02); *A61B 2090/365* (2016.02)

(58) Field of Classification Search
  USPC ........ 600/407, 410, 416, 424–429; 606/102; 345/418–420, 581, 589, 619, 620, 625
  See application file for complete search history.

(56) References Cited

U.S. PATENT DOCUMENTS

| | | | |
|---|---|---|---|
| 5,722,978 A | 3/1998 | Jenkins, Jr. | |
| 5,880,976 A | 3/1999 | DiGioia, III et al. | |
| 6,021,343 A | 2/2000 | Foley et al. | |
| 6,205,411 B1* | 3/2001 | DiGioia, III | A61B 17/15 623/901 |
| 6,385,475 B1 | 5/2002 | Cinquin et al. | |
| 6,466,815 B1* | 10/2002 | Saito | A61B 1/0005 600/109 |
| 6,533,737 B1 | 3/2003 | Brosseau et al. | |
| 6,554,837 B1 | 4/2003 | Hauri et al. | |
| 6,608,628 B1 | 8/2003 | Ross et al. | |
| 6,711,432 B1 | 3/2004 | Krause et al. | |
| 6,725,082 B2 | 4/2004 | Sati et al. | |
| 7,227,981 B1 | 6/2007 | Fleute et al. | |
| 7,239,908 B1 | 7/2007 | Alexander et al. | |
| 7,689,014 B2 | 3/2010 | Abovitz et al. | |
| 7,715,602 B2* | 5/2010 | Richard | A61B 90/36 382/128 |
| 7,799,077 B2 | 9/2010 | Lang et al. | |
| 7,842,092 B2 | 11/2010 | Otto et al. | |
| 7,881,768 B2 | 2/2011 | Lang et al. | |
| 2003/0216669 A1* | 11/2003 | Lang | A61B 5/4528 600/587 |
| 2004/0015070 A1 | 1/2004 | Liang et al. | |
| 2004/0138754 A1* | 7/2004 | Lang | A61F 2/30756 623/20.14 |
| 2005/0101966 A1 | 5/2005 | Lavallee | |
| 2005/0256389 A1* | 11/2005 | Koga | A61B 5/103 600/407 |
| 2006/0015030 A1 | 1/2006 | Poulin et al. | |
| 2006/0039591 A1 | 2/2006 | Zettel et al. | |
| 2006/0094951 A1 | 5/2006 | Dean et al. | |
| 2006/0095047 A1 | 5/2006 | de la Barrera | |
| 2008/0077003 A1 | 3/2008 | Barth et al. | |

FOREIGN PATENT DOCUMENTS

| | | |
|---|---|---|
| FR | 2785517 | 5/2000 |
| WO | 9500075 | 1/1995 |
| WO | 9840037 | 9/1998 |
| WO | 9923956 | 5/1999 |
| WO | 9960939 | 12/1999 |

OTHER PUBLICATIONS

Office Action issued May 26, 2010 in U.S. Appl. No. 10/415,962.
Office Action issued Oct. 6, 2010 in U.S. Appl. No. 10/415,962.
Geste Medico-Chirurgical Assiste par Ordinateur G.M.C.A.O 2001, 2 pages.
Fleute, M., et al., "Incorporating a statistically based shape model into a system for computer-assisted anterior cruciate ligament surgery," Medical Image Analysis, (1999), 3(3): 209-222.
Office Action issued Oct. 7, 2011 in U.S. Appl. No. 11/955,160.
Office Action issued Mar. 31, 2011 in U.S. Appl. No. 11/955,160.
International Search Report issued Mar. 1, 2002 in International Application No. PCT/FR01/03423.
Keinzle T C et al., "Total Knee Replacement," IEEE Engineering in Medicine and Biology Magazine, IEEE Inc. NY, NY vol. 14, No. 3 (May 1, 1995) pp. 301-306.
Fleute, M. et al., "Building a complete surface model from sparse data using statistical shape models: Application to Computer Assisted Knee Surgery." MICCAI 1998 Springer-Verlag LNCS Series, pp. 880-887, Oct. 1998.
Fleute, M. et al., "Nonrigid 3D/2D registration of images using statistical models" MICCAI '99, Springer-Verlag LNCS Series 1679, pp. 138-147, Oct. 1999.
Taylor, R. "Computer Integrated Surgery" Chapter 32, MIT Press 1996, entitled "Computer-assisted spinal surgery using anatomy-based registration" pp. 434-437 by Lavallee, S., et al.
Office Action issued Jul. 22, 2014 in U.S. Appl. No. 13/540,134.
U.S. Office Action dated Dec. 23, 2011 in U.S. Appl. No. 12/621,155.
U.S. Office Action dated Jul. 29, 2016 in U.S. Appl. No. 14/982,221.

* cited by examiner

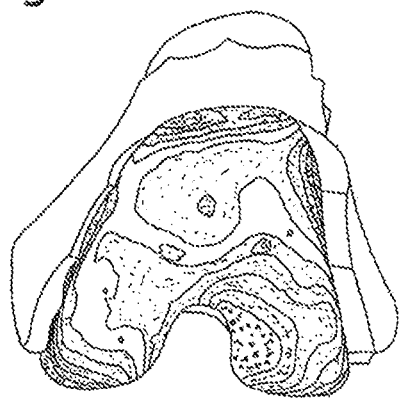
Fig. 3A
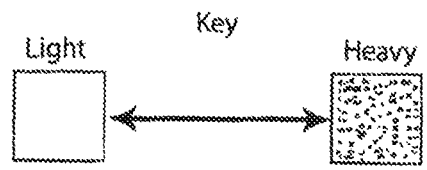
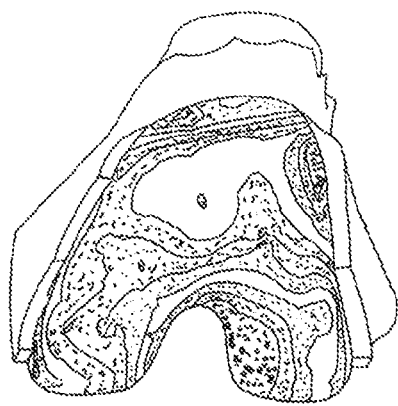
Fig. 3B
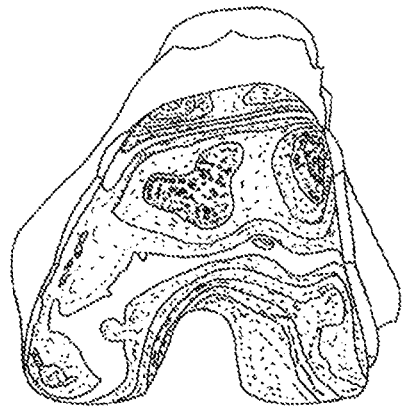
Fig. 3C

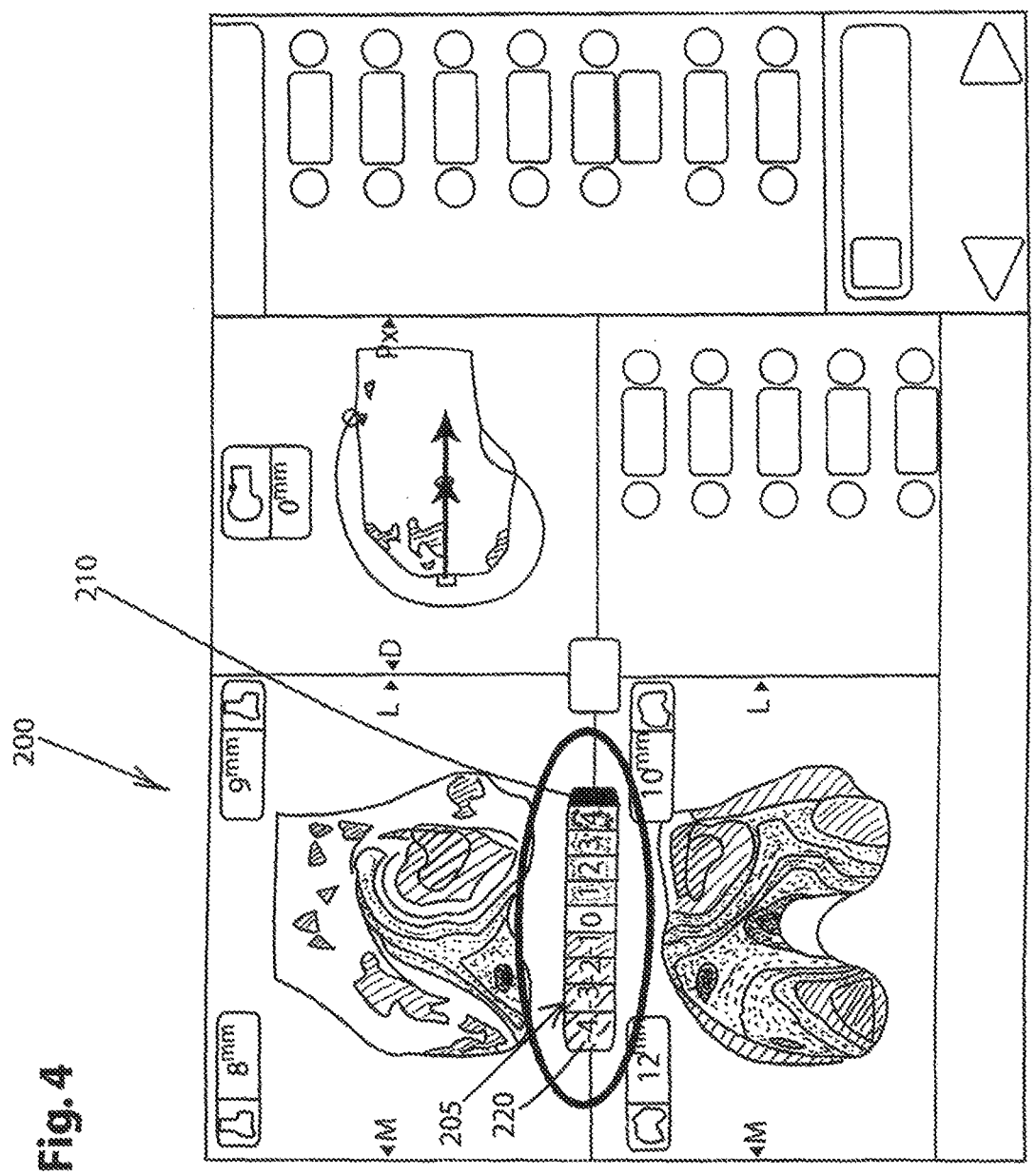

SYSTEM AND METHOD FOR DETERMINING AN OPTIMAL TYPE AND POSITION OF AN IMPLANT

CROSS-REFERENCE TO RELATED APPLICATION

The present application is a continuation of U.S. patent application Ser. No. 13/540,134 filed Jul. 2, 2012 which is a continuation of U.S. patent application Ser. No. 11/955,160 filed Dec. 12, 2007, which claims the benefit of U.S. patent application Ser. No. 60/869,668, filed Dec. 12, 2006, the entire disclosures of which is are hereby incorporated by reference herein in its their entirety.

TECHNICAL FIELD

The present invention relates to a method and system for computerized planning of implant surgery and in particular, relates to a system for assisting a surgeon to analyze and select the optimal position and type of prosthesis to install in a patient, by use of a computer, a model of the joint or bone to be fitted with the implant, and a database of available implants.

BACKGROUND

There exists on the market today several thousands of different shapes and sizes of prostheses for any given joint. Each of these implants has advantages and disadvantages with respect to many different criteria, such as, fulfillment of specific patient requirements including joint stability, function and performance, and proper sizing and fitting with the patients' joint morphology. Implants that are also tailored to specific genders or races are available (e.g., the Asian knee).

Currently, surgeons must rely on their intuition and their knowledge of the different performance characteristics and shapes of each available implant in order to try to best match it to the patient.

In particular, there is a lack of existing tools to help the surgeon accurately and efficiently determine which implant type or shape and which implant position best matches their patient's anatomy.

Computer assisted orthopaedic surgery has been developed to help the surgeon plan and execute joint replacement and resurfacing operations. These systems can use models of bones taken from pre-operative or intra-operative image data (for example CT's, MRI, Ultrasound, fluoroscopy, . . . ), or they can use image free techniques, such as, Bone Morphing where a model is deformed to points acquired on a surface of a bone. Alternatively, a hybrid approach can be used in which a pre-established model can be warped or morphed to acquired image data to aid in the model building process. Several publications exist in the literature describing the various techniques and just a few of them are listed:

Lavallee—System for determining the position of a knee prosthesis US20050101966; and
Fluete—Restoring of three-dimensional surfaces by using statistical models U.S. Pat. No. 7,227,981.

Each of the above listed references is hereby incorporated by reference in its entirety.

Different planning systems also exist to aid the surgeon in determining the optimal position and size of the prosthesis. These systems generally work by measuring different dimensions of the bone in different areas and comparing these with the corresponding dimensions of a particular size of one type of implant from a range of sizes of the same implant type.

A disadvantage of the existing systems for joint implant surgery is that, although they help the surgeon in selecting what size of prosthesis to install, they do not provide any significant assistance in determining which type of implant and/or which implant position provides the best fit to the patents anatomy. They do not help the surgeon identify how the subtleness of a particular prosthesis shape or prosthesis position fits the detailed and specific anatomy of the patient. This can be important for restoring optimal joint function and kinematics. In particular, femoral component rotation in knee arthroplasty is a key issue that can affect femoro-tibial and femoro-patellar kinematics. However, current systems primarily use only basic references (axes) and/or knee gap measurements to determine femoral rotation. They do not help the surgeon in an intuitive way to visualize how a particular change in the prosthesis position/rotation impacts the joint surfaces.

SUMMARY

The present invention relates to a method and system for implanting at least one prosthesis in a joint. The invention aids the surgeon in determining the optimal type, size, and position by taking into consideration the morphology and the function parameters of the involved joint as well as the external shape of the particular implants.

In one aspect of the invention, a computer-assisted orthopaedic surgery (CAOS) system is provided and is configured for performing joint reconstruction or resurfacing procedures on a patient, such as those performed in knee surgery. The system includes a position measurement device in communication with a computer to determine the position and orientation of objects in a three dimensional coordinate system. The three dimensional coordinate system includes at least one bone, such as the patient's femur or tibia. Objects to be tracked comprise at least one marker, which can be configured to emit, receive, or reflect energy, such as, light, electromagnetic, or acoustic energy.

To sense the position of light reflecting markers, the system includes at least two detecting elements, such as, two cameras. The two cameras detect the light reflected from the light reflecting markers to determine the position of each marker associated with an object to be tracked. Based on the respective positions of markers associated with the tracked object, the position and orientation of the tracked object are determined.

The system preferably includes a plurality of reference bodies that can be used to determine the position and orientation of a patient's bone. The reference bodies can be rigid members having at least three markers each. Each reference body preferably includes an attachment element, such as a screw or pin, with which the reference bodies can be attached to a bone. For example, respective reference bodies can be attached to the femur and tibia.

The system also can include a pointer. The pointer includes markers that allow the position and orientation of the pointer to be determined. The system also includes a calibration device that can be used to measure the relationship between the pointer tip and the markers. Thus, the position of the pointer tip can be determined from the positions of the markers relative to the three-dimensional coordinate system.

The computer can be configured to determine the position and orientation of the reference bodies and pointer based upon the position and orientation of the associated markers. Moreover, the system can be configured for identifying and applying an anatomical coordinate system to at least two bones of the joint. The anatomical coordinate system can include directions such as medial-lateral, proximal-distal, anterior-posterior, and so on.

In a further aspect, the present invention can provide a system for determining intra-operatively the three dimensional shape of the bone surface in the vicinity of the articulating joint and in particular in the vicinity of the prosthesis implantation area associated with the joint. In particular, the three dimensional shapes of the involved bones may be provided with image-free or image-based techniques.

In another aspect, the present invention can provide a system for measuring the relative positions of one bone with respect to another bone, and for determining the intra-articular space between the two bones at various positions and orientations of the joint.

In yet another aspect, the present invention can provide a system that determines and proposes an optimal implant type, size and position simultaneously from a database of implants.

In yet another aspect, the present invention can provide a system that analyzes the external shape of an implant and compares that to the morphology of the bone in which the prosthesis is to be implanted, and in particular in the vicinity of the implantation site.

In yet another aspect, the present invention can provide a system that aligns the position of an implant such that the external surface of the implant best fits the original anatomy of the patient's joint surface in certain critical areas.

In yet another aspect, the present invention can provide a system that distinguishes between the 'normal' and pathological or worn parts of a bone.

And in yet another aspect, the present invention can provide a system that displays numerically and graphically on a screen the difference between the morphology of the bone and the shape of the implant using a map such as a color or intensity map.

And in yet another aspect, the present invention can provide a system that displays numerically and graphically on a screen the difference between the morphology of the bone and the shape of the implant using different display representations for the normal and pathological areas of the joint.

Still further, the present invention can provide a system for displaying in real time the position and orientation of a surgical cutting guide or tool in relation to the targeted implant position and orientation.

According to one embodiment, a computer assisted orthopaedic surgery system for joint reconstruction or resurfacing includes a system for determining an optimal type, size and location of an implant to be implanted in at least one bone of a joint. The system includes a position determining device that is capable of tracking the movement of at lease one bone using a reference body that is attached to the bone and a pointer that has a tip for contacting a surface of the bone to capture one or more points on the surface. The system further includes a computer that is configured to determine the global morphology of the bone, and to determine which areas of the morphology are pathologic and which are normal. The system further includes a method for comparing the external surfaces of the implant to the normal bone morphology in order to select an optimal implant type from a database of available implants and/or to optimally position the implant.

These and other features and aspects of the invention can be appreciated from the accompanying figures and the following description.

BRIEF DESCRIPTION OF THE DRAWING FIGURES

Figure 2:
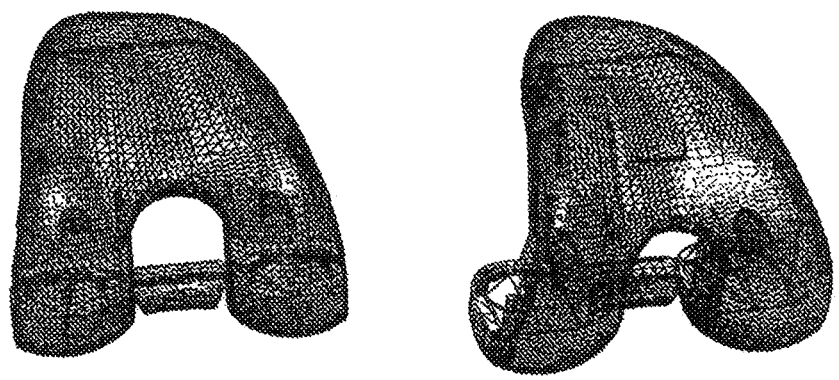
FIG. 2 is perspective view of an exemplary implant file for use in a system according to the present invention.

FIGS. 3A-C are perspective views of the implant file of FIG. 2 superimposed on a bone model in three different positions with various maps; and FIG. 4 is a planning page of the software application allowing adjustment of the implant type, size and position.

DETAILED DESCRIPTION OF PREFERRED EMBODIMENTS

The following description provides an example of how the present invention can be used in the case of total knee arthroplasty; however, the present invention is not limited to this one surgical application and can be used in any number of other orthopaedic procedures, such as total or partial knee, hip, elbow, shoulder arthroplasty or resurfacing.

A system according to the present invention is configured to permit the surgeon to plan the optimal, position, size, and type of prosthesis taking into account multiple criteria. This planning is performed prior to making some or all of the bone cuts necessary to insert and accommodate the implant components and in particular, the system and components thereof are used as tools in the overall planning package that provides numerical and graphic information to the surgeon to ensure optimal selection and placement of the implant components.

A) Description of Navigation System

Figure 1:
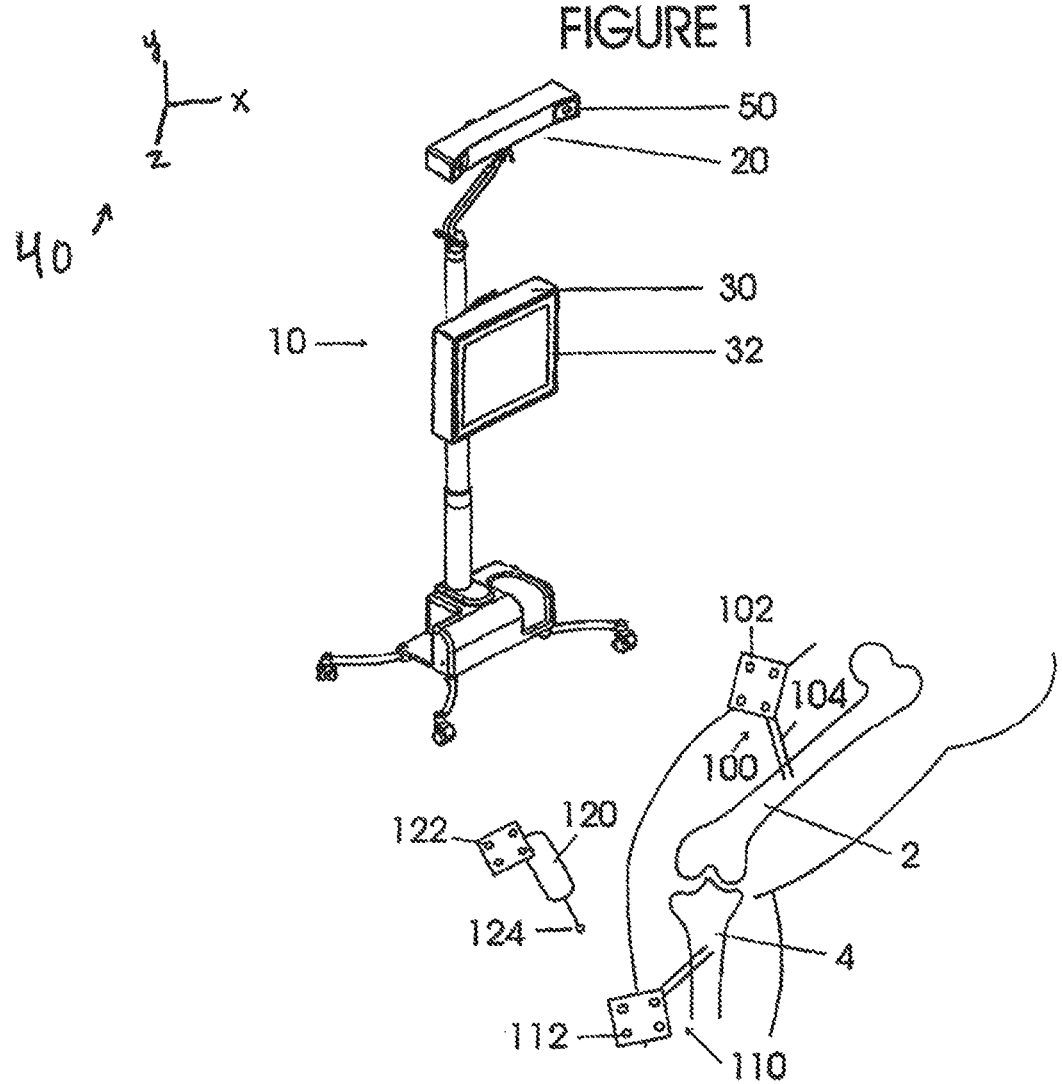
FIG. 1 is a perspective view of a computer-assisted orthopaedic surgery (CADS) system.

The overall system includes a navigation component (tool) and in particular, a navigation system. Referring now to FIG. 1, a computer-assisted orthopaedic surgery (CAOS) system 10 is schematically shown. The CAOS system 10 is configured for performing joint replacement or resurfacing surgeries, such as knee or hip replacement surgery. The system 10 includes a suitable position measuring device 20 that can accurately measure the position of marking elements in three dimensional space. The position measuring device 20 can employ any type of position measuring method as may be known in the art, for example, emitter/detector or reflector systems including optic, acoustic or other wave forms, shape based recognition tracking algorithms, or video-based, mechanical, electromagnetic and radio frequency systems.

In a preferred embodiment, schematically shown in FIG. 1, the position measuring system 20 is an optical tracking system that includes at least one camera that is in communication with a computer system 30 and is positioned to detect light reflected from a number of special light reflecting markers such as spheres or discs 50.

Detecting and determining the position and orientation of an object is referred to herein as "tracking" the object. To provide precision tracking of objects, markers 50 can be rigidly connected together to form reference bodies, (e.g., 100, 110), and these reference bodies can be attached to bones, tools and other objects to be tracked. One such device that has been found to be suitable for performing the tracking function is the Polaris™ system from Northern Digital Inc., Ontario, Canada. However, other systems can be used also.

The position measurement device 20 is described in greater detail in a number of publications, including U.S. Pat. Nos. 5,564,437 and 6,725,082, both of which are incorporated by reference in their entirety.

The position of the patient's bones, such as the patient's femur 2 and the patient's tibia 4, can be determined and tracked by attaching reference bodies 100, 110, which include respective markers 102, 112, to the bones 2, 4, respectively. The reference bodies can be attached to bones or tools using pins or screws 104, 114, or various quick release mechanisms. The reference bodies can also be shaped in the form of numbers (e.g., "1", "2", "3" . . . ) or alphabetical letters, such as "F" for Femur, "T" for Tibia, "P" for pointer, and so on, so as to avoid confusion as to which reference body should be attached to which bone or tool.

The tracked objects and their relative positions can be displayed on a screen (display) that is connected to the computer system 30. In a preferred embodiment, the display is a touch screen which can also be used for data entry.

The position measurement device 20 includes a number of different tools that are used at different locations and perform different functions as the system 10 is operated to yield optimal joint reconstruction data and information. These tools include a pointer 120, with markers 122, which can be used to digitize points on the surfaces of the femur 2 and tibia 4:

The reference bodies 100, 110, can be used for determining the position and orientation of an individual's bone in a three dimensional coordinate system 40. The reference bodies 100, 110 are preferably rigid and the respective markers 102, 112 are preferably configured to reflect infrared light. Markers 102, 112 are sufficient to establish the position and orientation of the rigid bodies 100, 110 within the coordinate system 40.

B) Bone Model Building Procedure

An exemplary bone model building procedure includes the following steps: (1) morphing; (2) image matching; and (3) hybrid.

Using the computer navigation station 10 and the associated tools and reference bodies 100, 110, the surgeon can build or register surface models of the bones of the involved joint. Models of the joint can either be built using point based methods, image-free morphing based methods, or medical image-based methods, such as those described in patent applications and U.S. Pat. No. 6,385,475 to Cinquin et al, US20050101966 to Lavallee, and U.S. Pat. No. 6,205,411 to DiGioia et al. (all of which are incorporated herein by reference in their entirety). The surgeon can use these shape models to plan the type, size, and position of the implants to be installed, along with many other parameters, such as, the patents' kinematics and soft tissue envelope, or any other methods known in the state of the art, including those described in the abovementioned patents, which are hereby incorporated by reference in their entirety.

In a preferred embodiment of the present invention, three dimensional geometrical surface models of the bones are provided by image-free means. Preferably these models are obtained by adjusting a deformable model of the bone to points acquired on the bone surface. Examples of some known methods of carrying out this task can be found in the following references: (1) "Building a complete surface model from sparse data using statistical shape models: application to computer assisted knee surgery" by M. Fleute and S. Lavallée, published in Medical Image Computing And Computer-Assisted Intervention—MICCAI'98, Spinger-Verlag LNCS Series, pages 880-887, October 1998; (2) Fleute M, Lavallee S, Julliard R. Incorporating a statistically based shape model into a system for computer-assisted anterior cruciate ligament surgery. Medical Image Analysis. 1999 September; 3(3):209-22. However, other known methods of obtaining geometrical bone models in surgery exist and can be employed (for example, matching medical image data such as CT, MRI, etc, to points acquired with a pointer or an ultrasound probe). Each of the above listed references is hereby incorporated by reference in its entirety.

In particular, the three dimensional shapes of the involved bones may be provided with image free techniques, such as using bone morphing software which is capable of extrapolating very few range data to obtain a complete surface representation of an anatomical structure (e.g., a bone). The specific details of bone morphing are set forth in the above references but in general, a complete surface model is built from sparse data using statistical shape models. In particular, the model is built from a population of a number of specimen (points), such as femur or tibia points that are digitized. Data sets are registered together using an elastic registration method (e.g., the Szeliski and Lavallee method) based on octree-splines. Principal component analysis (PCA) is performed on a field of surface deformation vectors. Fitting this statistical model to a few points in performed by non-linear optimization. Results can thus be presented for both simulated and real data. This method is very flexible and can be applied to any structures for which the shape is stable.

In one preferred embodiment of the invention, representations of the femur and tibial bones, or a portion thereof, are displayed on the screen. These models move on the screen in real time based on the motion of tracked femur and tibia. In one preferred embodiment of the invention, the system guides the surgeon in manipulating the knee, by using the bone representations as visual aids. Knee manipulations can be preformed, preferably before the implants are installed, to quantify the original stability of the knee. For example, varus/valgus stress tests can be applied to the knee at various knee flexion angles (for example, at 0°, 20°, 70°) and the degree of laxity in each compartment or the change in alignment can be recorded for each measurement. The laxities can be recorded automatically during the manipulations on a single page since the computer can track the relative positions of the bone and in real time calculate the knee flexion angle and store the maximum change in alignment when the flexion angle is at or near a particular value (for example 20±5°). Thus the system is able to guide the surgeon in making kinematic measurements of flexion and rotations in order to quantify the soft tissues enveloping the knee joint. The system is also capable of recording knee gap measurements at various knee angles, such as in extension (0°) and flexion (90°) with the knee joint distracted, so as tension is applied to the ligaments and the maximum joint spaces are quantified. Such systems are described in references such as and storing these values to be used as inputs in the implant planning algorithm As mentioned previously, the patients' bone model is used as an input into the implant planning algorithm. These models are typically in the form of a point or meshed based surface model consisting of points or nodes and polygons, such as triangles.

A database of 3D implant models in the form of 3D meshed surface are also used as inputs. These models describe the detailed external and internal shape of the implant, where the internal shape corresponds to the surface that is in contact with the host bone. For each implant model, specific characteristics are provided, such as antero-posterior size, medio-lateral width, 5 or 8 or more cut planes, implant peg positions and diameters, outer contours, specific discriminating areas in the form of a subset list of triangles from the meshed surface, specific surface curvature or thickness. This list of geometrical or surface data relative to the specificity of the implant is not exhaustive and can be provided by the implant manufacturer.

In one exemplary embodiment, the invention provides a system for planning the position and size of a prosthesis based on any criteria including those mentioned below, or simply manual selection and positioning by the surgeon. Once an initial implant size and shape is selected and displayed on the screen, the system can indicate to the surgeon the difference in shape between the external surface of the implant and the external surface of the bone based on the model of the bone and of the implant. This can be effectively accomplished by superimposing a map on the bone or implant displayed on the screen that depicts this difference. Different spectrums of color or transparences can be used to illustrate the map.

In one embodiment, an optimization process exists to find in the implant data base the model which provides a best fit to the patient bone model. This algorithm is tailored according to a list of specific target criteria, ranked with a priority and a tolerance range.

These criteria can be of different categories, including: (1) Geometrical criteria: axis alignment (for example, alignment to the mechanical axis of the leg), specific angle orientation, specific cut height distances, and so on; (2) Matching criteria: Alignment or centering of one implant with respect to another implant in the same joint; (3) Functionality criteria: equal internal and external joint gaps (i.e. ligament balancing), cut parallelism (for example, between the tibial plateau cut and distal or posterior femoral cuts), no residual laxity or a laxity inferior to a specific threshold; (4) Morphology matching criteria: no medio-lateral overhanging (for example, adjacent to one or more of the five femoral cuts such as the distal or anterior cut), anterior cortex tangency, surface matching in specific areas, trochlear groove orientation, fitting and opening, fitting of the implant perimeter with respect to the bone contour around the bone cuts made to implant the prosthesis.

These criteria are ranked with priority and a tolerance range is determined, according to the specificity of the implant system.

The unknowns of the optimization problem for each implant are: (1) The implant type; (2) The implant size; and (3) The implant position: 3 translations+3 rotations.

The system of the present invention includes the morphological shape of the implant compared to the shape of the anatomical bone surface in the optimization process in order to find the best fitting implant type, size and position.

The morphological comparison between the implant 3D model and the bone 3D model can take place for any of the optimization criterion.

In one embodiment, the system is used to help the surgeon position a femoral component for total knee arthroplasty such that the trochlear groove of the implant best matches the trochlear groove of the patient anatomy. In particular, the surgeon can manually fine-tune the rotational (axial) alignment and anterior/posterior positioning of the implant with respect to multiple criteria, including boney landmarks (transepicondylar axis, posterior condylar axis, or White-side's line) and gap criteria (medial and lateral flexion gaps) while simultaneously visualizing the influence of the positioning on the matching of the external surface of the implant to the patents femoral groove using the map.

EXAMPLES

The flexion of the implant is such that the femoral component anterior cut is parallel to the bone anterior cortex surface, within the range of −3° and +5°.

The femoral component axial rotation is such that the posterior condyles are parallel to the tibia cut for the balanced flexion position, but the orientation of the implant trochlear groove must stay within +/−2° from the orientation of the anatomical trochlear groove. The anatomic trochlear groove can be determined by searching for the line at the deepest part of the groove in the bone model, or by asking the surgeon to draw this line with pointer.

The implant position is based on geometrical alignment criteria, but the size must be chosen so that the distance between the implant model and the bone model is minimized on the anterior and on the posterior surfaces.

The global optimization algorithm is as follows:
For each implant type t (ex: t1=standard, t2=gender)
For each implant size s (ex: from size A to size E)
P(t,s)=Optimize (Implant_Model_t_s, rotation criteria, translation criteria, list of constraints).
Discriminating_Score(t,s)=Scores (P(t,s), Morpholocial_Discriminating_Criteria)
If Discriminating_Score(t,s)<Optimum_Score,
Then Optimum_Score=Discriminating_Score(t,s)
And Optimum_Solution=(t, s, P(t,s)).

The final output is the couple (t,s) and its corresponding position P(t,s) which are the optimum solution proposal.

The "Optimize" computation is based on a regular minimization process, starting with an initial proposal, and modifying the solutions in the direction of the gradient of cost functions for each of 6 position parameters. Such optimization processes exist and are commonly known in the state of the art, such as the so-called Levenberg-Marquardt algorithm (for example see http://en.wikipedia.org/wiki/Levenberg-Marquardt algorithm).

The cost functions are mathematical expressions of the target criteria. For geometrical criteria expressed directly in the terms of target angles or target distances, the mathematical formulation is trivial because there is directly a target numerical value.

For functionality criteria, the cost functions have to be translated in terms of angles differences or distances differences which have to be minimized.

For morphology matching criteria, the cost functions are translated in terms distances between surfaces, which have to be minimized.

The computation of the cost function value or discriminating score based on morphological shape mainly consists in the computation of a mean squared distance between two surfaces in predetermined areas.

Specific surface patches are defined on each implant 3D mesh as triangles subsets. For example, a list of triangles can represent the trochlear groove, another set can represent the medial anterior area and anther one the lateral anterior area of the implant. In other words the algorithm calculates the mean squared distance between predefined zones on the implant and bone surfaces, such as the femoral groove areas, the medial and lateral portions of the anterior flange, or the condyles. Obviously this could be extended to other surfaces of other joints, such as the hip joint (for example the femoral neck and head surfaces, or the acetabular fossa and rim).

The distance from the implant surface patch to the bone surface can be computed from any known algorithm for surface distance computation. Finally from all the distances computed with the triangles in the implant surface patch, the Root Mean Square is computed and this gives the discriminating score for that particular patch. Any particular subsets of nodes within a surface patch may also have different weighting scores associated with them, so that particular zones within the patches may have a greater or lesser influence on the overall score for that patch.

The final score can be computed from the RMS scores for all the determined patches, with further possible different weightings for each patch. The optimum solution is the one with the minimum discriminating score.

The user will have the feedback on the score value for the optimized solution (t, s, P(t,s)), but also for the other combinations for comparison.

Also, not only numerical feedback will be given, but a representation of the scoring factors through some graphical visualization to help the surgeon interpret the numerical results. As illustrated in FIG. 4, this representation can be based on distance map visualization 200, enabling the surgeon to differentiate the areas with a good morphology matching (distance of the implant 3D mesh to the bone 3D mesh close to 0), from the areas where the implant surface is above or under the bone surface.

For example, in a series of consecutive sizes, the optimization process gives the following distance map: the scale can go from dark blue where the implant surface is above the bone surface (indicated at 210 in FIG. 4 and also represented by the number 4 in the key 205 of FIG. 4) to light red where the implant surface is below the bone surface (indicated at 220 in FIG. 4 and also represented by the number −4 in the key 205). Light green colors can indicate the areas where surface of the implant most closely match the bone morphology (represented by the number 0 in the key 205 in FIG. 4). The number scale from negative four (−4) to positive four (+4) can correspond to the distance in millimeters that the implant is either inside or outside the bone surface, respectively, where the number zero (0) is a perfect match. By visualizing the degree of match, the map 205 thus provides an easy to use system for the surgeon to determine the best fit between the implant and the bone. For purpose of illustration, In FIGS. 3A-C, the areas with a higher concentration of stippling represent greater distances of the implant to the bone surface either inside or outside the bone surface, while areas with no stippling represent areas where a close fit exists between the implant and the bone. Areas of a lighter concentration of stippling represent areas where the implant is a lesser distance either outside or inside the bone surface as depicted in the key 205 which is a color map in one embodiment where different colors represent different degrees of distance from the implant to the bone surface.

In another embodiment of the invention, the system can also take into account which areas of the bone are worn or abnormal (pathological), and treat these areas of the bone differently in the optimization algorithm or in the display of the map. For example, worn areas could have a lower weighting or can be excluded completely for the optimization area. The map could be not shown or indicated by different colors or transparencies in those areas. Determination of normal and/or pathological areas of the bone can be done in any number ways, including:

Asking the surgeon to identify with the pointer;
Using surface curvature and shape of the bone itself;
By comparing the reconstructed bone surface with the generic morphing model using only global and not local deformation;
Identify areas which have undergone the most important deformations from the generic morphing model once the bone morphing has been performed;
Using the modes of variation;
By comparing it to the contra-lateral joint (for example, when pre-operative or intra-operative imaging is performed);
Using information of the measured kinematics (e.g. laxity); and
By using the relative bone orientations and global anatomy such as the mechanical axis to predict worn areas.

The determination of the optimal implant type, size and position taking into account the bone morphology in different areas and with different constraints can be also accomplished by:

Determining initially a subset of optimal implant sizes and positions for different implant types and then choosing the particular implant type that minimizes the difference between the bone surface and external implant surface in specific local areas;
Providing global numerical values such as the average and maximum deviation between the bone and the model in certain areas for a subset of implants in the database, to help the surgeon select which implant to use;
Find the best fitting implant type, size and position minimizing the distances between the bone shape and external implant shape while maintaining functional constraints such as alignment to the mechanical axis, troclear groove, epicondylar axis rectangular flexion spaces, patellar trajectory, etc.;
Using the ratio of width to AP dimension to best match the implant to the bone;
Using the contours of the virtual cuts compared to the contours of the implant cuts (especially the shape of the anterior cut contours);
Matching the AP dimension with the implant size and then selecting the implant that minimize the degree of overhang or exposed bone at the perimeter of the implant for at least two different types;
Using contralateral joint if not worn (image based); and
Using the patients gender or race as an initial input to selecting which prosthesis types to compare.

Additional methods of displaying on the screen the difference in the morphology of the native bone and the shape of the implant using a color map include:

Color proportional to distance;
Implant in semitransparent color superimposed over bone surface with the shade of transparency proportional to the distance to the bone;
"scanner-like slices" in sagittal, frontal and axial planes showing the profile of the bone and the profile of the implant external surface;
using the direction normal to the implant or bone surface;
In some cases the bone may also protrude from the implant which can also be represented in different color or tone than for bone which is inside the prosthesis;
Using different representations for areas of the bone model that are normal and pathological;
Using different representations for areas of the Bone Morphing Model that are not accurate; and Displaying difference between operated knee and contralateral knee morphology taking into account worn and not worn surfaces.

It will therefore be appreciated that the differences between the two displayed models, namely, the implant model selected from the database (FIG. 2) and the bone model derived from an imaging operation (FIGS. 3A-C), such as bone morphing, are superimposed on one another with differences between the two models being visually highlighted so as to permit a surgeon, etc., to immediate and in real-time determine the degree of "fit" between the two models as shown in FIGS. 3A-C. For example, the differences, which reflect a degree of distance where the implant model departs from the bone model in localized areas, can be illustrated using a color map to show the relative degree of differences. In a more intense color can be used to show regions where the two models depart the greatest and a less intense color can be used to show a closer fit between the two models. More areas with greater intensities mean the fit between the selected model and the bone model is not particularly good. Instead of using color intensities, other visual means, including different colors, can be used to shown the varying degree of fit between the two models. FIGS. 3A-C are perspective views of the implant file superimposed on a bone model in three different positions with various maps to show the degree of fit between the selected model and the bone model. In FIGS. 3A-C, the areas with a higher concentration of stippling represent areas where the two models depart the greatest, while areas with no stippling represent areas where a close (good) fit exists between the two models. Areas of a lighter concentration of stippling represent an intermediate fit between the two models.

One advantage of the present system is that the user (surgeon) can load a model of a different implant model from the database and display in real time in a superimposed manner over the bone model to determine the relative degree of fit between the two. This ability to select amongst a group of stored implant models in the database, allows the surgeon to very quickly compare and evaluate a number of different implants to see which implant offers the most optimal fit for the patient in view of the patient's bone structure as displayed by the bone model.

What is claimed is:

1. A computer-assisted surgery system for planning a joint replacement procedure comprising a computer having stored in a memory:
    a 3D computer bone model; and
    a 3D computer bone replacement implant model,
    wherein the computer includes instructions stored in the memory and executable by a processor to optimize an overlay fit of a portion of an external surface of the 3D computer bone replacement implant model to a corresponding portion of an external surface of the 3D computer bone model by alignment of said portions.

2. The system of claim 1, wherein the computer further includes instructions stored in the memory and executable by the processor to perform a minimization process to minimize distances between the external surface of the 3D computer bone replacement implant model and the corresponding external surface of the 3D computer bone model to align said portions.

3. The system of claim 1, wherein the external surface of the 3D computer bone replacement implant model and the 3D computer bone model is at least one of a distal femur, a trochlear groove, and a condylar surface.

4. The system of claim 1, wherein the computer further includes instructions stored in the memory and executable by the processor to optimize the fit by at least one of a geometric criteria, a matching criteria, a functional criteria, and a morphology criteria.

5. The system of claim 4, wherein the geometric criteria includes at least one of alignment of a mechanical axis of a leg, a bone resection cut height, and an orientation angle of joint bones.

6. The system of claim 4, wherein the matching criteria includes alignment or centering of one implant with respect to another implant in a joint.

7. The system of claim 4, wherein the functional criteria includes at least one of equal internal and external joint gaps, cut parallelism between a tibial plateau cut and a femoral cut, and laxity.

8. A computer-assisted surgery system for planning a joint replacement procedure comprising a computer having stored in a memory:
    a 3D computer model of a bone having an articulating surface; and
    a 3D computer implant model of a replacement of the bone,
    wherein the computer is configured to optimize an overlay matching of an articulating surface of the 3D computer implant model with the articulating surface on the 3D computer bone model.

9. The system of claim 8, wherein the computer is further configured to optimize a fit of the 3D computer bone replacement implant model on the 3D computer bone model based on a target criteria being one of a geometric criteria and a functional criteria.

10. The system of claim 8, wherein the articulating surface matching includes aligning a portion of an external surface of the 3D computer bone replacement implant model to a corresponding portion of an external surface of the 3D computer bone model.

11. The system of claim 10, wherein the computer is configured to perform a minimization process to minimize distances between the external surface of the 3D computer bone replacement implant model and the corresponding external surface of the 3D computer bone model to align said portions.

12. The system of claim 10, wherein the external surface of the 3D computer bone replacement implant model and the 3D computer bone model is at least one of a distal femur, a trochlear groove, and a condylar surface.

13. The system of claim 9, wherein the geometric criteria includes at least one of alignment of a mechanical axis of a leg, a bone resection cut height, and an orientation angle of joint bones.

14. The system of claim 8, wherein the computer is further configured to align or center one implant model with respect to another implant model in a joint.

15. The system of claim 9, wherein the functional criteria includes at least one of equal internal and external joint gaps, cut parallelism between a tibial plateau cut and a femoral cut, and laxity.

16. A method of planning a joint replacement procedure using a computer-assisted surgery system comprising:
    generating a 3D computer bone model of a patient; and
    optimizing an overlay fit of a 3D computer bone replacement implant model on the 3D computer bone model by matching a portion of an external surface of the 3D computer bone replacement implant model that functionally replaces a corresponding portion of an external surface of the 3D computer bone model.

17. The method of claim 16, wherein the step of optimizing includes performing a minimization process to minimize distances between the external surface of the 3D computer bone replacement implant model and the corresponding external surface of the 3D computer bone model to align said portions.

18. The method of claim 16, wherein the external surface of the 3D computer bone replacement implant model and the 3D computer bone model is at least one of a distal femur, a trochlear groove, and a condylar surface.

19. The method of claim 16, further comprising optimizing the fit by at least of alignment of a mechanical axis of a leg, a bone resection cut height, an orientation angle of joint bones, equal internal and external joint gaps, cut parallelism between a tibial plateau cut and a femoral cut, laxity, and alignment or centering of one implant with respect to another implant in a joint.

* * * * *